(12) United States Patent
Yoon

(10) Patent No.: US 6,495,686 B2
(45) Date of Patent: Dec. 17, 2002

(54) PYRIMIDO [4,5,B]INDOLIZINE DERIVATIVES AND AZA ANALOGUES THEREOF; CRF1 SPECIFIC LIGANDS

(75) Inventor: Taeyoung Yoon, Guilford, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/791,370

(22) Filed: Feb. 23, 2001

(65) Prior Publication Data

US 2002/0019525 A1 Feb. 14, 2002

Related U.S. Application Data

(63) Continuation of application No. 09/328,179, filed on Jun. 8, 1999, now Pat. No. 6,194,574.
(60) Provisional application No. 60/088,808, filed on Jun. 9, 1998.

(51) Int. Cl.[7] .................. C07D 471/14; C07D 487/14
(52) U.S. Cl. .................. 544/250; 540/467; 540/470; 540/481; 540/544; 540/553; 540/575; 540/600; 544/3; 544/55; 544/60; 544/63; 544/96; 544/115
(58) Field of Search .................. 544/250; 514/267

(56) References Cited

U.S. PATENT DOCUMENTS

| | | | |
|---|---|---|---|
| 3,932,431 A | 1/1976 | Walter | 260/290 R |
| 3,988,338 A | 10/1976 | Skoog et al. | 260/256.5 R |
| 4,605,642 A | 8/1986 | Rivier et al. | 514/12 |
| 5,063,245 A | 11/1991 | Abreu et al. | 514/404 |
| 5,244,896 A | 9/1993 | Borcherding et al. | 514/258 |
| 5,378,700 A | 1/1995 | Sakuma et al. | 514/212 |
| 5,644,057 A | 7/1997 | Yuan et al. | 544/280 |
| 5,804,685 A | 9/1998 | Yuan et al. | 544/335 |
| 5,847,136 A | 12/1998 | Yuan et al. | 544/280 |
| 6,020,492 A | 2/2000 | Yuan et al. | 544/250 |

FOREIGN PATENT DOCUMENTS

| | | |
|---|---|---|
| EP | 0 239 191 A | 9/1987 |
| EP | 0 770 080 | 7/1999 |
| JP | 10114744 A | 5/1998 |
| WO | WO 94/13676 A1 | 6/1994 |
| WO | WO 95/10506 A | 4/1995 |
| WO | WO 96/35689 * | 11/1996 |
| WO | WO 98/08847 | 3/1998 |

OTHER PUBLICATIONS

A. Buschauer, Archiv. Der Pharmazie, vol. 322, No. 3, 1989, pp. 165–171.
A. R. Katrizzky et al., Journal of Chemical and Engineering Data, vol. 32, No. 4, 1987, pp. 479–481.
A. Rakeeb Deshmukh et al., Heterocycles, vol. 34, No. 6, 1992, pp. 1239–1249.
F. Herold et al., Journal of Heterocyclic Chemistry., vol. 36, No. 2, 1999, pp. 389–396.
F. Sauter et al., Journal of Chemical Research. Synopses, No. 7, 1977, pp. 186.
K. Posselt, Arzneim. Forsch., vol. 28, 1978, pp. 1056–1065.
M. Cardellini et al., Farmaco, vol. 42, No. 4, 1987, pp. 307–317.
Montgomery et al., J. Het. Chem., vol. 9, 1972, pp. 1077–1079.
Owens et al., Pharmacological Reviews, vol. 43, No. 4, 1991, pp. 425–473.
R. J. Wolters et al., Journal of Pharmaceutical Sciences., vol. 64, No. 12, 1975, pp. 2013–2014.
Shiraishi et al., Chemical Abstracts, vol. 128, No. 25, 1998, p. 591.
Y.M. Volovenko et al., Khim. Geterotsikl. Soedin., vol. 6, 1991, p. 85.

* cited by examiner

*Primary Examiner*—Deepak R. Rao
(74) *Attorney, Agent, or Firm*—McDonnell Boehnen Hulbert & Berghoff

(57) ABSTRACT

Disclosed are compounds of the formula:

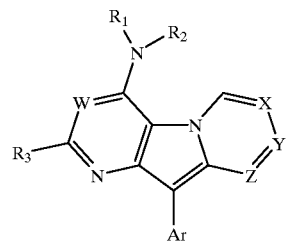

wherein Ar, $R_1$, $R_2$, $R_3$, W, X, Y, and Z are substituents as defined herein, which compounds are highly selective partial agonists or antagonists at human $CRF_1$ receptors and are useful in the diagnosis and treatment of treating stress related disorders such as post traumatic stress disorder (PTSD) as well as depression, headache and anxiety.

9 Claims, No Drawings

US 6,495,686 B2

PYRIMIDO [4,5,B]INDOLIZINE DERIVATIVES AND AZA ANALOGUES THEREOF; CRF1 SPECIFIC LIGANDS

This is a continuation of application Ser. No. 09/328,179, filed Jun. 8, 1999, now U.S. Pat. No. 6,194,574 which claims benefit of U.S. Provisional application Ser. No. 60/088,808, filed Jun. 9, 1998.

BACKGROUND OF THE INVENTION

1. Field of the Invention

This invention relates to pyrido[2,3-b]indolizine derivatives and aza analogues thereof that selectively bind to corticotropin-releasing factor (CRF) receptors. It also relates to pharmaceutical compositions comprising such compounds. It further relates to the use of such compounds in treating stress related disorders such as post traumatic stress disorder (PTSD) as well as depression, headache and anxiety.

2. Description of the Related Art

Posselt, K., Arzneim.-Forsch. 1978, 28, 1056–65, describe the synthesis of 10-(4-methoxyphenyl)pyrido[2,3-b]indolizine. Volovenko et al., Khim. Geterotsikl. Soedin. 1991, 6, 852, describe the synthesis of 2-chloro and 2-methylthio-10-tosylmethylpyrimido[4,5-b]indolizine.

SUMMARY OF THE INVENTION

This invention provides novel compounds of Formula I which interact with CRF receptors.

In one aspect, the invention provides pharmaceutical compositions comprising compounds of Formula I. In another aspect, it provides compositions useful in treating stress related disorders such as post traumatic stress disorder (PTSD) as well as depression, headache and anxiety. These compositions include a compound of Formula I. Further, in a third aspect, the invention provides methods of treating such stress related disorders.

Accordingly, a broad aspect of the invention is directed to compounds of Formula I:

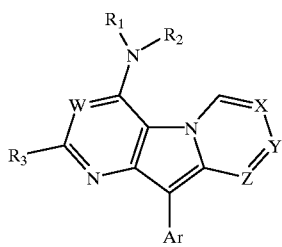

I

Ar is phenyl, 1- or 2-naphthyl, 2-, 3-, or 4-pyridyl, 2- or 3-thienyl, 4- or 5-pyrimidyl, each of which is optionally mono-, di-, or trisubstituted with halogen, trifluoromethyl, hydroxy, amino, mono- or di($C_1$–$C_6$) alkyl amino, carboxamido, $C_1$–$C_6$ alkyl, $C_3$–$C_7$ cycloalkyl, or $C_1$–$C_6$ alkoxy, with the proviso that at least one of the positions ortho or para to the point of attachment of Ar to the tricyclic ring system is substituted;

$R_1$ and $R_2$ independently represent
  $C_1$–$C_6$ alkyl;
  $C_3$–$C_7$ cycloalkyl;
  $C_3$–$C_7$ cycloalkyl($C_1$–$C_6$)alkyl;
  $C_1$–$C_6$ alkoxy($C_1$–$C_6$)alkyl; or
  aryl($C_1$–$C_6$)alkyl where aryl is phenyl, 1- or 2-naphthyl, 2-, 3-, or 4-pyridyl, 2- or 3-thienyl or 2-, 4 or 5-pyrimidyl, each of which is optionally mono- or disubstituted with halogen, hydroxy, $C_1$–$C_6$ alkyl, $C_3$–$C_7$ cycloalkyl, $C_1$–$C_6$ alkoxy, or ($C_1$–$C_6$ alkylene)—A—$R_4$, wherein A is O, S, NH, or N($C_1$–$C_6$ alkyl) and $R_4$ is hydrogen, $C_3$–$C_7$ cycloalkyl, or $C_1$–$C_6$ alkyl; or $R_1$ and $R_2$ taken together represent —$(CH_2)_n$—A—$(CH_2)_m$— wherein n is 2, 3 or 4, A is methylene, oxygen, sulfur, or $NR_5$, wherein $R_5$ is hydrogen, $C_3$–$C_7$ cycloalkyl, or $C_1$–$C_6$ alkyl, and m is 0, 1, or 2;

$R_3$ is $C_1$–$C_6$ alkyl, or ($C_1$–$C_6$ alkylene)—G—$R_6$, wherein G is O, S, NH, or N($C_1$–$C_6$ alkyl) and $R_6$ is hydrogen, $C_3$–$C_7$ cycloalkyl, or $C_1$–$C_6$ alkyl; and W, X, Y, and Z are independently N or C—$R_7$, wherein $R_7$ is hydrogen, $C_3$–$C_7$ cycloalkyl, or $C_1$–$C_6$ alkyl.

These compounds are highly selective partial agonists or antagonists at CRF receptors and are useful in the diagnosis and treatment of stress related disorders such as post traumatic stress disorder (PTSD) as well as depression and anxiety.

Another aspect of the invention is directed to intermediates useful in the preparation of the compounds of Formula I.

In a further aspect, the invention provides methods for making the compounds of Formula I and the intermediates for preparing such compounds.

DETAILED DESCRIPTION OF THE INVENTION

Preferred compounds of Formula I are those where Ar is phenyl substituted in the 2, 4, and 6 positions, preferably with methyl, ethyl or propyl; naphthyl substituted in the 2 and 6 positions, preferably with methyl, ethyl or propyl; or 3-pyridyl substituted in the 2, 4, and 6 positions, preferably with methyl, ethyl or propyl; 5-pyrimidiyl substituted in the 2, 4, and 6 positions, preferably with methyl, ethyl, or propyl. Particularly, preferred components of Formula I include those where the Ar group is substituted in the 2 and 6 or the 2, 4, and 6 positions with methyl.

Preferred compounds of the invention have Formula II:

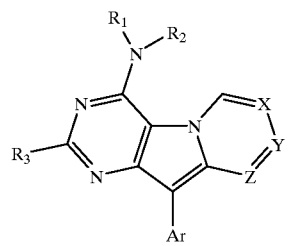

II wherein Ar, $R_1$, $R_2$, and $R_3$ are as defined above for Formula I; and

X, Y, and Z are independently N or C—$R_7$, wherein $R_7$ is hydrogen, $C_3$–$C_7$ cycloalkyl, or $C_1$–$C_6$ alkyl.

Preferred compounds of Formula II are those where X and Z are both CH and Y is CH or nitrogen. More preferred compounds of Formula II are those where $R_3$ is $C_1$–$C_4$ alkyl or $C_3$–$C_6$ cycloalkyl($C_1$–$C_3$)alkyl. Other more preferred compounds of Formula II are those where $R_1$ and $R_2$ independently represent $C_1$–$C_6$ alkyl, $C_3$–$C_7$ cycloalkyl ($C_1$–$C_6$)alkyl, —$(CH_2)_2O(CH_2)_2$—; and Ar is phenyl trisubstituted with $C_1$–$C_3$ alkyl in the 2, 4, and 6 positions relative to the point of attachment of Ar to the tricyclic ring system. Particularly preferred compounds of the Formula II are those where Ar is phenyl trisubstituted with methyl in the 2, 4, and 6 positions relative to the point of attachment of Ar to the tricyclic ring system.

Other particularly preferred compounds of Formula II are those where X, Y and Z are all CH.

Other preferred compounds of the invention have Formula III

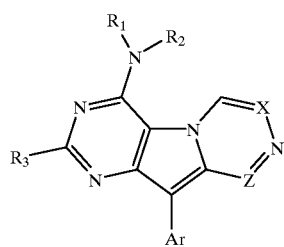

III wherein Ar, $R_1$, $R_2$, and $R_3$ are as defined above for Formula I; and

X and Z are independently N or C—$R_7$, wherein $R_7$ is hydrogen, $C_3$–$C_7$ cycloalkyl, or $C_1$–$C_6$ alkyl More preferred compounds of Formula III are those where $R_3$ is $C_1$–$C_4$ alkyl or $C_3$–$C_6$ cycloalkyl($C_1$–$C_3$)alkyl. Other more preferred compounds of Formula III are those where $R_1$ and $R_2$ independently represent $C_1$–$C_6$ alkyl, $C_3$–$C_7$ cycloalkyl($C_1$–$C_6$)alkyl, —$(CH_2)_2O(CH_2)_2$—; and Ar is phenyl trisubstituted with $C_1$–$C_3$ alkyl in the 2, 4, and 6 positions relative to the point of attachment of Ar to the tricyclic ring system. Particularly preferred compounds of the Formula III are those where Ar is phenyl trisubstituted with methyl in the 2, 4, and 6 positions relative to the point of attachment of Ar to the tricyclic ring system.

Still other preferred compounds of the invention have formula:

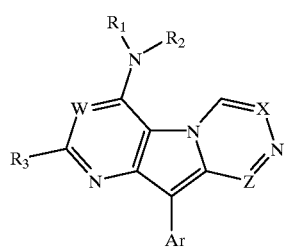

IV wherein wherein Ar, $R_1$, $R_2$, and $R_3$ are as defined above for Formula I; and W, X, and Z are independently N or C—$R_7$, wherein $R_7$ is hydrogen, $C_3$–$C_7$ cycloalkyl, or $C_1$–$C_6$ alkyl.

Preferred compounds of Formula IV are those where X and Z are both CH.

More preferred compounds of Formula IV are those where $R_3$ is $C_1$–$C_4$ alkyl or $C_3$–$C_6$ cycloalkyl($C_1$–$C_3$)alkyl. Other more preferred compounds of Formula IV are those where $R_1$ and $R_2$ independently represent $C_1$–$C_6$ alkyl, $C_3$–$C_7$ cycloalkyl($C_1$–$C_6$)alkyl, —$(CH_2)_2O(CH_2)_2$—; and Ar is phenyl trisubstituted with $C_1$–$C_3$ alkyl in the 2, 4, and 6 positions relative to the point of attachment of Ar to the tricyclic ring system. Particularly preferred compounds of the Formula IV are those where Ar is phenyl trisubstituted with methyl in the 2, 4, and 6 positions relative to the point of attachment of Ar to the tricyclic ring system.

Other particularly preferred compounds of IV are those where W is CH and X and Z are both CH.

Yet other preferred compounds of the invention have formula:

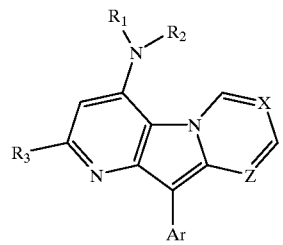

V wherein Ar, $R_1$, $R_2$, and $R_3$ are as defined above for Formula I; and

X and Z are independently N or C—$R_7$, wherein $R_7$ is hydrogen, $C_3$–$C_7$ cycloalkyl, or $C_1$–$C_6$ alkyl.

Preferred compounds of Formula V are those where $R_3$ is $C_1$–$C_4$ alkyl or $C_3$–$C_6$ cycloalkyl($C_1$–$C_3$)alkyl. Other more preferred compounds of Formula V are those where $R_1$ and $R_2$ independently represent $C_1$–$C_6$ alkyl, $C_3$–$C_7$ cycloalkyl ($C_1$–$C_6$)alkyl, —$(CH_2)_2O(CH_2)_2$—; and Ar is phenyl trisubstituted with $C_1$–$C_3$ alkyl in the 2, 4, and 6 positions relative to the point of attachment of Ar to the tricyclic ring system. Particularly preferred compounds of the Formula V are those where Ar is phenyl trisubstituted with methyl in the 2, 4, and 6 positions relative to the point of attachment of Ar to the tricyclic ring system.

The invention also provides intermediates useful in preparing compounds of Formula I. These intermediates have Formulae VI–X.

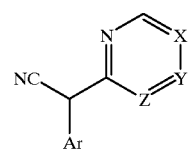

VI where Ar, and X, Y and Z are defined as above for Formula I.

Preferred compounds of Formula VI are those where Y is CH or N and X and Z are CH, and Ar is phenyl trisubstituted with $C_1$–$C_3$ alkyl in the 2, 4, and 6 positions relative to the point of attachment of Ar to the methylene group. Particularly preferred compounds of the Formula VII are those where Y is CH or N, X and Z are CH, and Ar is phenyl trisubstituted with methyl in the 2, 4, and 6 positions relative to the point of attachment of Ar to the methylene group.

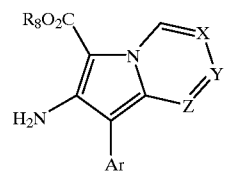

VII where $R_8$ is $NH_2$ or N=$C(R_3)C(R_7)$ where $R_3$ and $R_7$ are as defined above for Formula I; and Ar, and X, Y and Z are defined as above for Formula I.

Preferred compounds of Formula VII are those where Y is CH or N and X and Z are CH, and Ar is phenyl trisubstituted with $C_1$–$C_3$ alkyl in the 2, 4, and 6 positions relative to the point of attachment of Ar to the bicyclic ring system. Particularly preferred compounds of the Formula VII are those where Y is CH or N; X and Z are CH; and Ar is phenyl trisubstituted with methyl in the 2, 4, and 6 positions relative to the point of attachment of Ar to the bicyclic ring system.

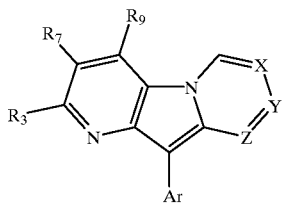

VIII where $R_9$ is halogen or hydroxy; and $R_3$, $R_7$, Ar, and X, Y and Z are defined as above for Formula I.

Preferred compounds of Formula VIII are those where Y is CH or N; X and Z are CH; and Ar is phenyl trisubstituted with $C_1$–$C_3$ alkyl in the 2, 4, and 6 positions relative to the point of attachment of Ar to the tricyclic ring system. Particularly preferred compounds of the Formula VIII are those where Y is CH or N; X and Z are CH; and Ar is phenyl trisubstituted with methyl in the 2, 4, and 6 positions relative to the point of attachment of Ar to the tricyclic ring system.

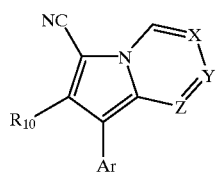

IX where $R_{10}$ is $NH_2$ or $NHC(O)R_3$, where $R_3$ is as defined above for Formula I; and Ar, and X, Y and Z are defined as above for Formula I.

Preferred compounds of Formula IX are those where Y is CH or N; X and Z are CH; and Ar is phenyl trisubstituted with $C_1$–$C_3$ alkyl in the 2, 4, and 6 positions relative to the point of attachment of Ar to the bicyclic ring system. Particularly preferred compounds of the Formula IX are those where Y is CH or N; X and Z are CH; and Ar is phenyl trisubstituted with methyl in the 2, 4, and 6 positions relative to the point of attachment of Ar to the bicyclic ring system.

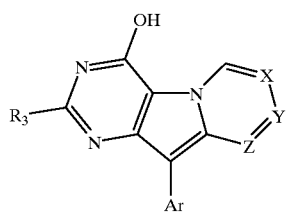

X where $R_3$, Ar, X, Y and Z are defined as above for Formula I.

Preferred compounds of Formula X are those where Y is CH or N; X and Z are CH; and Ar is phenyl trisubstituted with $C_1$–$C_3$ alkyl in the 2, 4, and 6 positions relative to the point of attachment of Ar to the tricyclic ring system. Particularly preferred compounds of the Formula X are those where Y is CH or N; X and Z are CH; and Ar is phenyl trisubstituted with methyl in the 2, 4, and 6 positions relative to the point of attachment of Ar to the tricyclic ring system.

In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)$n—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

Where a compound exists in various tautomeric forms, the invention is not limited to any one of the specific tautomers. The invention includes all tautomeric forms of a compound.

By "$C_1$–$C_6$ alkyl" or "lower alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred $C_1$–$C_6$ alkyl groups are methyl, ethyl, propyl, butyl, cyclopropyl and cyclopropylmethyl.

By "$C_1$–$C_6$ alkoxy" or "lower alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By the term "halogen" in the present invention is meant fluorine, bromine, chlorine, and iodine.

Representative pyrido[2,3-b]indolizine derivatives and their aza analogues of the present invention are shown in Table 1. The number below each compound is its compound number.

TABLE 1

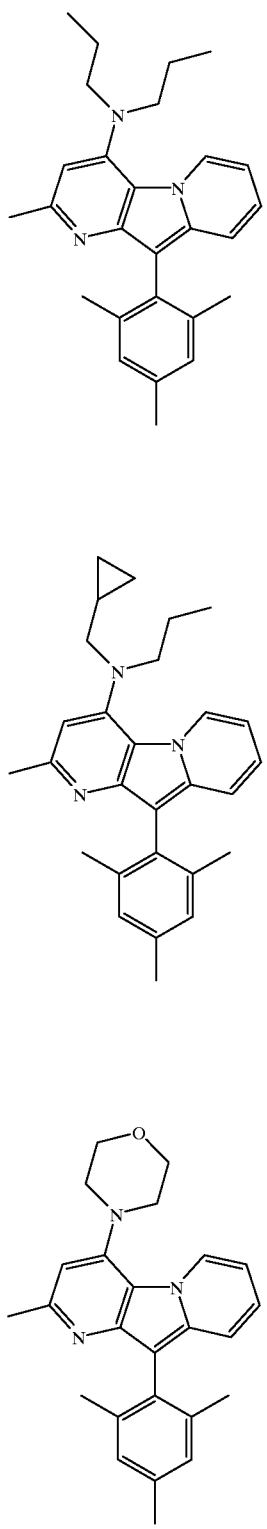

TABLE 1-continued

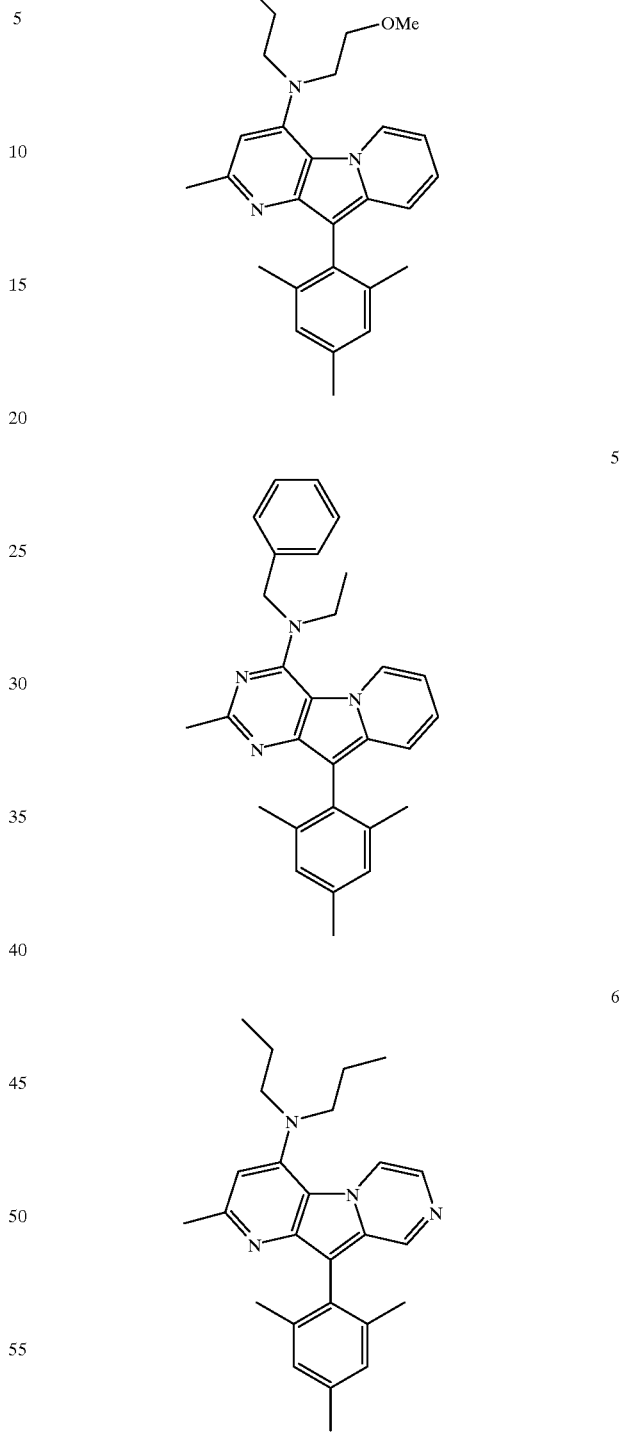

The interaction of compounds of the invention with CRF receptors is shown in the examples. This interaction results in the pharmacological activities of these compounds as illustrated in relevant animal models.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

The preparation of the pyrido[2,3-b]indolizines and aza analogues thereof of the present invention is illustrated in Schemes I and II. Those having skill in the art will recognize that the starting materials may be varied and additional steps employed to produce compounds encompassed by the present invention.

In Scheme I, the variables Ar, $R_1$, $R_2$, $R_3$, $R_7$, X, Y, and Z are defined as above for Formula I.

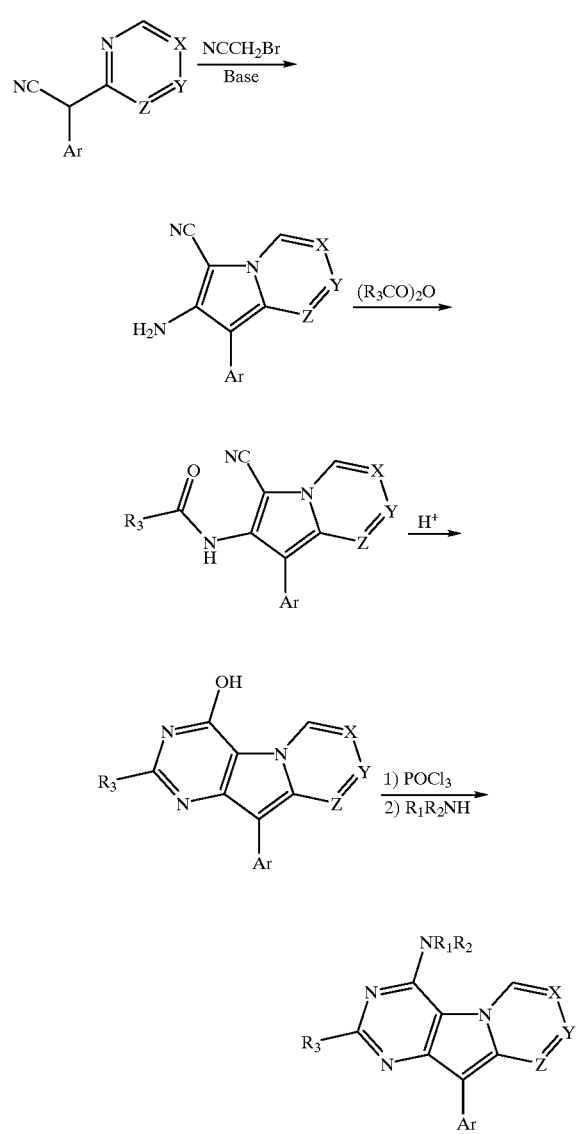

In Scheme I, the variables Ar, $R_1$, $R_2$, $R_3$, X, Y, and Z are defined as above for Formula I.

The disclosures of all articles and references mentioned in in this application, including patents, are incorporated herein by reference.

The preparation of the compounds of the present invention is illustrated further by the following examples which are not to be construed as limiting the invention in scope or spirit to the specific procedures and compounds described in them.

Commercial reagents were used without further purification. DMSO refers to dimethyl sulfoxide. THF refers to tetrahydrofuran. DMF refers to dimethylformamide. Room temperature refers to 20° to 25° C. Concentration in vacuo implies the use of a rotary evaporator. Chromatography refers to flash column chromatography performed using 32–63 mm silica gel. Proton NMR chemical shifts are reported in parts per million (d) relative to tetramethylsilane as an internal standard.

EXAMPLE 1

A. 2-(2-Pyridinyl)-2-(2,4,6-trimethylphenyl)ethanenitrile

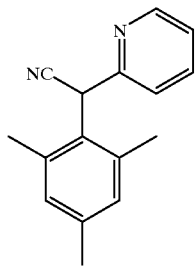

A mixed solution of 2-(2,4,6-trimethylphenyl) ethanenitrile (20 g; 0.126 mol) and 2-bromopyridine (35 g; 0.22 mol) in DMSO (25 mL) is added to a solution of potassium t-butoxide (35 g; 0.31 mol) dissolved in DMSO (125 mL) dropwise slowly over a 1-hour period. After the addition, the mixture is further stirred for 4 hours at room temperature and then slowly poured into a stirred, ice-cold solution of ammonium chloride with vigorous stirring. The resulting tan precipitate is filtered, pressed, washed with methanol, and air-dried to give 20 g of the title compound as a pale yellow solid (67%): [1]H nmr (400 MHz, CDCl$_3$) d 2.30 (s, 6 H), 2.32 (s, 3 H), 5.76 (s, 1 H), 6.93 (s, 2 H), 7.12 (d, 1 H), 7.21 (dd, 1 H), 7.63 (t, 1 H), 8.63 (d, 1 H).

B. Ethyl 2-amino-1-(2,4,6trimethylphenyl)indolizine-3-carboxylate

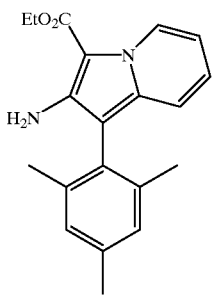

Ethyl bromoacetate (23 mL; 0.21 mol) is added slowly dropwise over a 3-hour period to a mixture of 2-(2-pyridinyl)-2-(2,4,6-trimethylphenyl)-ethanenitrile (22.3 g; 0.094 mol) and potassium carbonate (78 g; 0.57 mol) suspended in DMSO (100 mL). The mixture is stirred for 1 day, poured into an aqueous ammonium chloride solution (ca. 1 L), and extracted with three 200 mL portions of ethyl ether. Combined extracts are washed with saturated brine, dried (Na$_2$SO$_4$), filtered, and concentrated in vacuo. The residue is dissolved in THF (200 mL), cooled to 0° C., and potassium t-butoxide (12 g; 0.11 mol) is added slowly in portions over a 10-minute period. After 30 minutes at 0° C., the mixture is diluted with aqueous ammonium chloride and extracted twice with 150 mL portions of 50% ethyl ether in hexane. The combined extracts are washed with saturated brine, dried (Na$_2$SO$_4$), filtered, concentrated in vacuo, and chromatographed (5 to 10% ethyl acetate in hexane) to give 19.2 g of the title compound as an oil (63%): [1]H nmr (400 MHz, CDCl$_3$) d 1.47 (t, 3 H), 2.06 (s, 6 H), 2.35 (s, 3 H), 4.46 (br q, 2 H), 6.6 (br t, 1 H), 6.75 (d, 1 H), 6.9 (br t, 1 H), 7.00 (s, 2 H), 9.4 (br 1 H).

C. 4-Hydroxy-2-methyl-10-(2,4,6-trimethylphenyl)pyrido[2,3-b]-indolizine

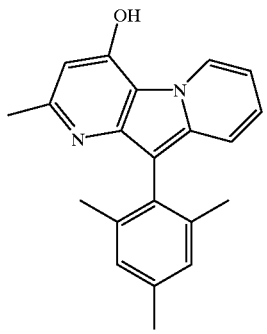

To a solution of 2-amino-3-ethoxycarbonyl-1-(2,4,6-trimethylphenyl)-indolizine (19.2 g; 59.6 mmol) in 2,2-dimethoxypropane (100 mL) is added di-camphorsulfonic acid (0.2 g). The mixture is stirred at reflux for 30 minutes and then distilled slowly to remove ca. 60 mL of volatiles over a 30-minute period. The solution is cooled to ambient temperature under an inert atmosphere, diluted with anhydrous toluene (50 mL), and concentrated in vacuo. The residue is dissolved in toluene (50 mL) and to the stirred solution is then added a 0.5 M solution of potassium bis(trimethylsilyl)amide in toluene (250 mL; 125 mmol) dropwise over a 1-hour period. After the addition is complete, the mixture is further stirred for 2 hours at room temperature before being concentrated in vacuo to a small volume and then diluted with aqueous ammonium chloride. The resulting emulsion-like biphasic mixture is suction-filtered and washed succesively with water, methanol, and ethyl ether. Air- and vacuum drying provides 10.1 g of the title compound as a pale yellow solid (54%).

D. 4–Chloro-2-methyl-10-(2,4,6-trimethylphenyl)pyrido[2,3-b]-indolizine

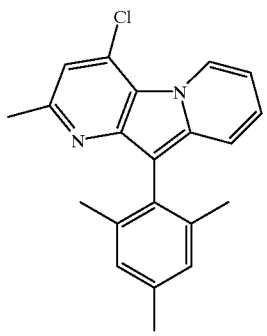

A solution of 4-hydroxy-2-methyl-10-(2,4,6-trimethylphenyl)pyrido-[2,3-b]indolizine (10.1 g; 32 mmol) in phosphorus oxychloride (60 mL) is heated at 100° C. for 1 hour, cooled to room temperature, and concentrated in vacuo. The residue is partitioned into ice water and dichloromethane. The aqueous phase is separated and extracted twice with dichloromethane. The combined organics are washed with a 1 N aqueous sodium hydroxide solution and then with water. The solution is dried (Na$_2$SO$_4$), filtered, and concentrated in vacuo, and the resulting dark residue is filtered through a short pad of silica gel and washed with 25% ethyl acetate in hexane. The filtrate is concentrated in vacuo to give 10.1 g of the title compound as a yellow solid (94%): $^1$H nmr (400 MHz, CDCl$_3$) d 2.00 (s, 6 H), 2.37 (s, 3 H), 2.64 (s, 3 H), 6.58 (t, 1 H), 6.95 (dd, 1 H), 7.00 (s, 2 H), 7.07 (s, 1 H), 7.08 (d, 1 H), 9.26 (d, 1 H).

E. 4-(N,N-Dipropyl)amino-2-methyl-10-(2,4,6-trimethylphenyl)-pyrido[2,3-b]indolizine

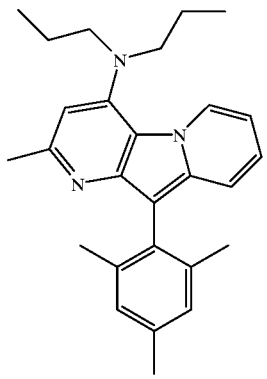

A mixture of 4-chloro-2-methyl-10-(2,4,6-trimethylphenyl)pyrido[2,3-b]indolizine (10.0 g; 30 mmol) and dipropylamine (15 mL; 1 mol) in DMSO (30 mL) is heated at 130° C. under nitrogen atmosphere for two days. The mixture is cooled to room temperature, diluted with water (ca. 300 mL), and extracted with ether (100 mL×2). The combined organics are washed successively with saturated ammonium chloride and saturated brine, dried (Na$_2$SO$_4$), filtered, and concentrated. The concentrate is chromatographed (first with 5% ethyl acetate in hexane and then with 10% triethylamine in hexane) to give 10.4 g of the title compound (compound 1, Table 1) as a fluorescent yellow foam (87%): $^1$H nmr (400 MHz, CDCl$_3$) d 0.90 (t, 6 H), 1.6 (br, 4 H), 2.02 (s, 6 H), 2.37 (s, 3 H), 2.62 (s, 3 H), 3.2 (br, 4 H), 6.52 (t, 1 H), 6.73 (s, 1 H), 6.89 (t, 1 H), 7.00 (s, 2 H), 7.06 (d, 1 H), 8.98 (d, 1 H).

The following compounds are prepared essentially according to the procedures set forth above in Example 1.

EXAMPLE 2

4-(N-Cyclopropanemethyl)propylamino-2-methyl-10-(2,4,6-trimethyl-phenyl)pyrido[2,3-b]indolizine (Compound 2; Table 1)

EXAMPLE 3

4-(1-Morpholino)-2-methyl-10-(2,4,6-trimethyl-phenyl) pyrido[2,3-b]indolizine (Compound 3; Table 1)

EXAMPLE 4

4-(N,N-Bis(2-methoxyethyl)amino)-2-methyl-10-(2,4,6-trimethyl-phenyl)pyrido[2,3-b]indolizine (Compound 4; Table 1)

EXAMPLE 5

A. 4-Hydroxy-2-methyl-10-(2,4,6-trimethylphenyl) pyrimido[4,5-b]indolizine

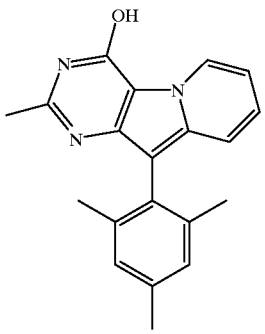

A solution of 2-amino-3-cyano-1-(2,4,6-trimethylphenyl) indolizine (220 mg) in an acetic anhydride (0.5 mL)—acetic acid (2 mL) mixture is heated at 100° C. for 1 hour. The mixture is cooled to room temperature and concentrated in vacuo. The residue is then heated in 85% phosphoric acid (5 mL) at 100° C. for 1.5 hours, allowed to cool to room temperature, diluted with water, and neutralized to pH 7 by adding aqueous ammonium hydroxide. The resulting yellow suspension is extracted twice with dichloromethane and the combined extracts are dried (Na$_2$SO$_4$), filtered, concentrated, and chromatographed (50% ethyl acetate in hexane to 10% methanol in ethyl acetate) to give 120 mg of the title compound as a yellow solid.

B. 4-Chloro-2-methyl-10-(2,4,6-trimethylphenyl) pyrimido[4,5-b]indolizine

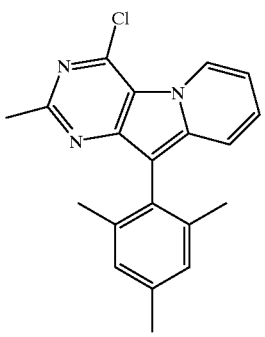

A solution of 4-hydroxy-2-methyl-10-(2,4,6-trimethylphenyl)pyrimido-[4,5-b]indolizine (120 mg) in phosphorus oxychloride (2 mL) is heated at 100° C. for 2 hours, cooled to room temperature, and concentrated in vacuo. The residue is partitioned into ice water and dichloromethane. The aqueous phase is separated and extracted twice with dichloromethane. The combined organic extracts are washed with a saturated sodium bicarbonate solution and subsequently dried (Na$_2$SO$_4$), filtered, and concentrated in vacuo. The resulting dark residue is chromatographed on silica gel (10% to 20% ethyl acetate in hexane) to give 54 mg of the title compound as a greenish yellow foam: $^1$H nmr (400 MHz, CDCl$_3$) d 1.99 (s, 6 H), 2.38 (s, 3 H), 2.79 (s, 3 H), 6.80 (m, 1 H), 7.00 (s, 2 H), 7.19 (m, 2 H), 9.27 (d, 1 H).

C. 4-(N-Benzylethylamino)-2-methyl-10-(2,4,6-trimethylphenyl)-pyrimido[4,5-b]indolizine

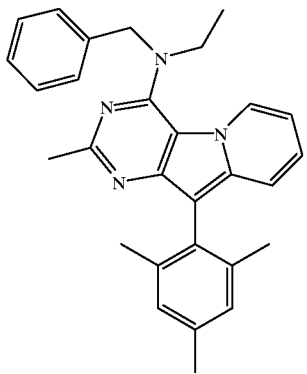

A mixture of 4–Chloro-2-methyl-10-(2,4,6-trimethylphenyl)pyrimido-[4,5-b]indolizine (15 mg) and N-benzylethylamine (0.04 mL) in DMSO (0.4 mL) is heated to 110° C. for 2 hours. The mixture is allowed to cool, diluted with aqueous ammonium chloride, and extracted twice with 50% ethyl ether in hexane. The combined extracts are washed with saturated brine, dried ($Na_2SO_4$), filtered, and concentrated in vacuo. Chromatography (10% to 20% ethyl acetate in hexane) gives 22 mg of the title compound (compound 5, Table 1) as a yellow oil: $^1H$ nmr (400 MHz, $CDCl_3$) d 1.17 (t, 3 H), 2.00 (s, 6 H), 2.38 (s, 3 H), 2.70 (s, 3 H), 3.40 (q, 2 H), 4.72 (s, 2 H), 6.68 (t, 1 H), 7.00 (s, 2 H), 7.03 (d, 1 H), 7.13 (d, 1 H), 7.29 (d, 1 H), 7.35 (t, 2 H), 7.41 (d, 2 H), 8.61 (d, 1 H).

The following compounds are prepared essentially according to the procedures set forth above in Example 5.

EXAMPLE 6

4-(N-Cyclopropanemethyl)propylamino-2-methyl-10-(2,4,6-trimethyl-phenyl)pyrimido[4,5-b]indolizine. (Compound 7)

EXAMPLE 7

4-(N,N-Bis-(2-methoxyethyl)amino)-2-methyl-10-(2,4,6-trimethyl-phenyl)pyrimido[4,5-b]indolizine. (Compound 8)

EXAMPLE 8

A. 2-Pyrazinyl-2-(2,4,6-trimethylphenyl)ethanenitrile

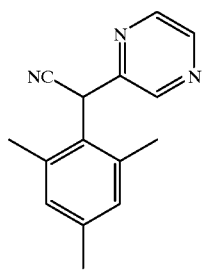

A mixture of 2-(2,4,6-trimethylphenyl)ethanenitrile (1.6 g) and chloro-pyrazine (1.6 g) in THF (6 mL) is slowly added dropwise to an ice-cold solution of potassium t-butoxide (3.4 g) in THF (10 mL). After the addition, the mixture is further stirred at 0° C. for 30 minutes and then diluted with aqueous ammonium chloride. The resulting mixture is extracted twice with ethyl ether and the combined extracts are washed with saturated brine, dried ($Na_2SO_4$), filtered, and concentrated in vacuo. Chromatography (20 to 33% ethyl acetate in hexane) gives 2.15 g of the title compound as a beige solid $^1H$ nmr (400 MHz, $CDCl_3$) d 2.30 (s, 9 H), 5.78 (s, 1 H), 6.95 (s, 2 H), 8.46 (s, 1 H), 8.54 (d, 1 H), 8.60 (d, 1 H).

B. Ethyl 2-amino-1-(2,4,6-trimethylphenyl)pyrrolo[1,2-a]pyrazine-2-carboxylate

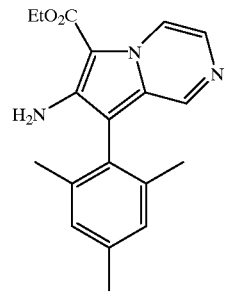

To a mixture of 2-pyrazinyl-2-(2,4,6-trimethylphenyl) ethanenitrile (1.6 g) and potassium carbonate (2.8 g) suspended in DMF (10 mL) at 0° C. is added a solution of ethyl bromoacetate (1.0 mL) in DMF (2 mL) slowly dropwise over a 15-minute period. After the addition, the mixture is further stirred at 0° C. for 1 hour, diluted with aqueous ammonium chloride, acidified with HCl to a pH of about 7. The resulting precipitate is filtered and air-dried to give 2.5 g of a dark, greenish solid. The solid is redissolved in THF (10 mL) and treated with potassium t-butoxide (1.0 M solution in THF, 7.5 mL) at 0° C. After 30 minutes, the mixture is diluted with aqueous ammonium chloride and extracted twice with ethyl ether. The combined extracts are washed with saturated brine, dried ($Na_2SO_4$), filtered, and concentrated in vacuo. Chromatography (20 to 33% ethyl acetate in hexane) gives 0.40 g of the title compound as a yellow oil: $^1H$ nmr (400 MHz, $CDCl_3$) d 1.48 (t, 3 H), 2.02 (s, 6 H), 2.38 (s, 3 H), 4.50 (q, 2 H), 4.6 (br, 2 H, $NH_2$), 7.01 (s, 2 H), 7.69 (d, 1 H), 8.25 (s, 1 H), 9.0 (br, 1 H).

C. 4-Hydroxy-2-methyl-10-(2,4,6-trimethylphenyl) pyrido-[2',3':4.5]pyrrolo[1,2-a]pyrazine

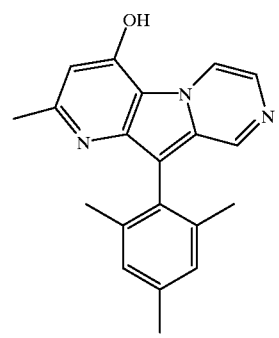

A catalytic amount of dl-camphorsulfonic acid is added to a solution of ethyl 2-amino-1-(2,4,6-trimethylphenyl) pyrrolo[1,2-a]pyrazine-2-carboxyl-ate (0.40 g) in 2,2-dimethoxypropane (10 mL) and the mixture is heated to reflux for 30 minutes. Over this period, about 5 mL of volatiles are removed by slow distillation; the remaining material is further refluxed for another 15 minutes. The mixture is cooled to room temperature and concentrated in vacuo. The residue is dissolved in THF (6 mL), cooled to 0° C. to the cooled solution is added dropwise a 1.0 M solution of sodium bis(trimethylsilyl)amide in THF (2.5 mL). After the addition, the deep red solution is allowed to warm to room temperature and stirred for 2 additional hours before being diluted with aqueous ammonium chloride and extracted with three portions of dichloromethane. The combined organic extracts are dried ($Na_2SO_4$), filtered, concentrated in vacuo, and triturated with hot ethyl acetate. The product, which precipitates upon cooling and dilution with ethyl ether, is filtered and air-dried (220 mg). The filtrate is concentrated in vacuo and another crystallization in minimal ethyl acetate and ether provides an additional 100 mg crop of the title compound as a light yellow solid: $^1$H nmr (400 MHz, $CDCl_3$) d 2.0 (s, 6 H), 2.38 (s, 3 H), 2.40 (s, 3 H), 6.14 (s, 1 H), 7.04 (s, 2 H), 7.81 (d, 1 H), 8.2 (br, 1 H), 8.60 (s, 1 H), 8.43 (d, 1 H).

D. 4–Chloro-2-methyl-10-(2,4,6-trimethylphenyl)pyrido[2',3':4,5]-pyrrolo[1,2-a]pyrazine

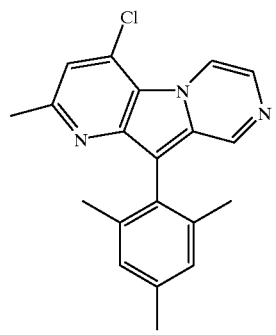

A solution of 4-Hydroxy-2-methyl-10-(2,4,6-trimethylphenyl)pyrido-[2',3':4,5]pyrrolo[1,2-a]pyrazine (220 mg) in phosphorus oxychloride (2 mL) is heated to 100° C. for 1 hour. The resulting dark tan solution is concentrated in vacuo, diluted with water, and neutralized by adding saturated sodium bicarbonate solution. The neutralized solution is extracted 3 times with dichloromethane and the combined extracts are dried ($Na_2SO_4$), filtered, concentrated, and chromatographed on silica gel (10 to 20% ethyl acetate in hexane) to give 120 mg of the title compound as a yellow foam: $^1$H nmr (400 MHz, $CDCl_3$) d 2.03 (s, 5 H), 2.38 (s, 3 H), 2.69 (s, 3 H), 7.03 (s, 2 H) 7.25 (s, 1 H), 7.66 (d, 1 H), 8.70 (s, 1 H), 9.00 (d, 1 H).

E. 4-(N,N-Dipropyl)amino-2-methyl-10-(2,4,6-trimethylphenyl)-pyrido[2',3':4,5]pyrrolo[1,2-a]pyrazine

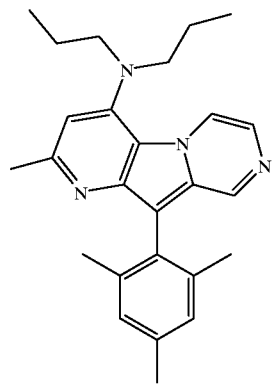

To a solution of 4–Chloro-2-methyl-10-(2,4,6-trimethylphenyl)pyrido-[2',3':4,5]pyrrolo[1,2-a]pyrazine (23 mg) in DMSO (0.5 mL) is added dipropylamine (0.1 mL) and the resulting mixture is heated at 130° C. for 3.5 days. The mixture is then allowed to cool to room temperature, diluted with aqueous ammonium chloride, and extracted twice with ethyl ether. The extracts are combined, washed with saturated brine, dried ($Na_2SO_4$), filtered, concentrated in vacuo, and chromatographed (10 to 20% ethyl acetate in hexane) to give 14.3 mg of the title compound (compound 6, Table 1) as a yellow, glassy oil: 0.90 (t, 6 H), 1.6 (m, 4 H), 2.03 (s, 6 H), 2.38 (s, 3 H), 2.62 (s, 3 H), 3.2 (br, 4 H), 6.81 (s, 1 H), 7.02 (s, 2 H), 7.60 (d, 2 H), 8.6 (m, 2 H).

The following compounds are prepared essentially according to the procedures set forth above in Example 8.

EXAMPLE 9

4-(1-Morpholino)-2-methyl-10-(2,4,6-trimethylphenyl) pyrido-[2',3':4,5]pyrrolo[1,2-a]pyrazine. (Compound 9)

EXAMPLE 10

4-(N,N-Bis-(2-methoxyethyl)amino)-2-methyl-10-(2,4,6-trimethyl-phenyl)pyrido-[2',3':4,5]pyrrolo[1,2-a]pyrazine. (Compound 10)

EXAMPLE 11

The pharmaceutical utility of compounds of the invention is indicated by the following assay.

Assay for CRF receptor binding activity

CRF receptor binding is performed using a modified version of the assay described by Grigoriadis and De Souza (Biochemical, Pharmacological, and Autoradiographic Methods to Study Corticotropin-Releasing Factor Receptors. Methods in Neurosciences, Vol. 5, 1991). Membrane pellets containing CRF receptors are resuspended in 50 mM Tris buffer pH 7.7 containing 10 mM $MgCl_2$ and 2 mM EDTA and centrifuged for 10 minutes at 48000 g. Membranes are washed again and brought to a final concentration of 150 mg/ml in binding buffer (Tris buffer above with 0.1% BSA, 15 mM bacitracin and 0.01 mg/ml aprotinin.). For the binding assay, 100 ml of the membrane preparation is added to 96 well microtube plates containing 100 ml of 125I-CRF (SA 2200 Ci/mmol, final concentration of 100 pM) and 50 ml of drug. Binding is carried out at room temperature for 2 hours. Plates are then harvested on a Brandel 96 well cell harvester and filters are counted for gamma emissions on a Wallac 1205 Betaplate liquid scintillation counter. Non-specific binding is defined by 1 mM cold CRF. $IC_{50}$ values are calculated with the non-linear curve fitting program RS/1 (BBN Software Products Corp., Cambridge, Mass.). The binding affinity for the compounds of the invention, expressed as an $IC_{50}$ value, generally ranges from about 0.5 nanomolar to about 10 micromolar.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

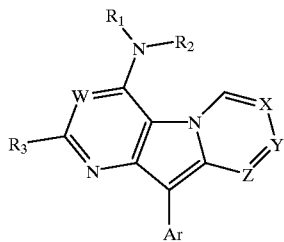

or the pharmaceutically acceptable salts thereof wherein:

Ar is phenyl, 1- or 2-naphthyl, 2-, 3-, or 4-pyridyl, 2- or 3-thienyl, 4- or 5-pyrimidyl, each of which is optionally mono-, di-, or trisubstituted with halogen, trifluoromethyl, hydroxy, amino, carboxamido, $C_1$–$C_6$ alkyl, $C_3$–$C_7$ cycloalkyl, or $C_1$–$C_6$ alkoxy, with the proviso that at least one of the positions ortho or para to the point of attachment of Ar to the tricyclic ring system is substituted;

$R_1$ and $R_2$ independently represent
  $C_1$–$C_6$ alkyl;
  $C_3$–$C_7$ cycloalkyl;
  $C_3$–$C_7$ cycloalkyl ($C_1$–$C_6$)alkyl;
  $C_1$–$C_6$ alkoxy($C_1$–$C_6$)alkyl; or
  aryl($C_1$–$C_6$)alkyl where aryl is phenyl, 1- or 2-naphthyl, 2-, 3-, or 4-pyridyl, 2- or 3-thienyl or 2-, 4 or 5-pyrimidyl, each of which is optionally mono- or disubstituted with halogen, hydroxy, $C_1$–$C_6$ alkyl, $C_3$–$C_7$ cycloalkyl, $C_1$–$C_6$ alkoxy, or ($C_1$–$C_6$ alkylene)—A—$R_4$, wherein A is O, S, NH, or N($C_1$–$C_6$ alkyl) and $R_4$ is hydrogen, $C_3$–$C_7$ cycloalkyl, or $C_1$–$C_6$ alkyl; or $R_1$ and $R_2$ taken together represent —$(CH_2)_n$—A—$(CH_2)_m$— wherein n is 2, 3 or 4, A is methylene, oxygen, sulfur, or $NR_5$, wherein $R_5$ is hydrogen, $C_3$–$C_7$ cycloalkyl, or $C_1$–$C_6$ alkyl, and m is 0, 1, or 2;

$R_3$ is $C_1$–$C_6$ alkyl; or ($C_1$–$C_6$ alkylene)—G—$R_6$, wherein G is O, S, NH, or N($C_1$–$C_6$ alkyl) and $R_6$ is hydrogen, $C_3$–$C_7$ cycloalkyl, or $C_1$–$C_6$ alkyl; and W is nitrogen, X, Y, and Z are independently C—$R_7$, wherein $R_7$ is hydrogen, $C_3$–$C_7$ cycloalkyl, or $C_1$–$C_6$ alkyl.

2. A compound according to claim 1, wherein W is nitrogen and X, Y, and Z are CH.

3. A compound according to claim 2, wherein $R_3$ is $C_1$–$C_4$ alkyl or $C_3$–$C_6$cycloalkyl($C_1$–$C_3$)alkyl.

4. A compound according to claim 3, wherein $R_1$ and $R_2$ independently represent $C_1$–$C_6$ alkyl, $C_3$–$C_7$ cycloalkyl ($C_1$–$C_6$)alkyl, or —$(CH_2)_2O(CH_2)_2$—.

5. A compound according to claim 4, wherein Ar is phenyl trisubstituted with $C_1$–$C_3$ alkyl in the 2, 4, and 6 positions relative to the point of attachment of Ar to the tricyclic ring system.

6. A compound according to claim 5, wherein Ar is phenyl trisubstituted with methyl in the 2, 4, and 6 positions relative to the point of attachment of Ar to the tricyclic ring system.

7. A compound according to claim 1 which is 4-(N-benzylethylamino)-2-methyl-10-(2,4,6-trimethylphenyl)pyrimido[4,5-b]indolizine.

8. A compound according to claim 1 which is 4-(N-cyclopropanemethyl)-propylamino-2-methyl-10-(2,4,6-trimethylphenyl)pyrimido[4,5-b]indolizine.

9. A compound according to claim 1 which is 4-(N,N-bis-(2-methoxy-ethyl)amino)-2-methyl-10-(2,4,6-trimethylphenyl)pyrimido[4,5-b]indolizine.

* * * * *